United States Patent
Kemperman et al.

(10) Patent No.: US 7,956,202 B2
(45) Date of Patent: Jun. 7, 2011

(54) **INTERMEDIATE COMPOUNDS FOR THE PREPARATION OF *TRANS*-5-CHLORO-2-METHYL-2,3,3A,12B-TETRAHYDRO-1*H*-DIBENZ[2,3:6,7]-OXEPINO[4,5-*C*]PYRROLE**

(76) Inventors: Gerardus Johannes Kemperman, Oss (NL); Jacobus Johannes Maria Van Der Linden, Oss (NL); Michael R. Reeder, Skillman, NJ (US)

( * ) Notice: Subject to any disclaimer, the term of this patent is extended or adjusted under 35 U.S.C. 154(b) by 0 days.

(21) Appl. No.: 12/632,513

(22) Filed: Dec. 7, 2009

(65) Prior Publication Data
US 2010/0152461 A1  Jun. 17, 2010

Related U.S. Application Data

(62) Division of application No. 11/399,142, filed on Apr. 6, 2006, now Pat. No. 7,872,147.

(60) Provisional application No. 60/669,422, filed on Apr. 7, 2005.

(51) Int. Cl.
*C07D 313/10* (2006.01)
(52) U.S. Cl. ......... 549/354; 549/200; 549/346; 548/421
(58) Field of Classification Search ........... 549/200, 549/346, 354; 548/421
See application file for complete search history.

(56) References Cited

U.S. PATENT DOCUMENTS

| 4,145,434 | A | 3/1979 | Van der Burg | |
|---|---|---|---|---|
| 7,750,167 | B2 * | 7/2010 | Kemperman et al. | 548/421 |
| 7,872,147 | B2 * | 1/2011 | Kemperman et al. | 548/421 |

FOREIGN PATENT DOCUMENTS

| JP | 49069697 | 7/1974 |
|---|---|---|
| WO | WO95/23600 | 9/1995 |
| WO | WO99/32108 | 7/1999 |

OTHER PUBLICATIONS

DeBoer et al., Org-5222"Antipsychotic Dopamine D2 Receptor Antagonist 5-HT2 Receptor Antagonist", Drugs of the Future, vol. 18, pp. 1117-1120, 1993.
Funke et al., Physico-Chemical Properties and Stability of Trans-5-Chloro-2-Methyl-2,3,3a,12b-Tetrahydro-1H-Dibenz [2,3;6,7]Oxepino[4,5-c]Pyrrolidine Maleate, Arzneim-Forsch, Drug Research, vol. 40, pp. 556-539, 1990.
Vader et al., "The Syntheses of Radiolabelled Org 52222 and its Main Metabolite Org 30526," Journal of Labelled Compounds and Radiopharm, vol. 34, pp. 845-869, 1994.
March et al., March's Advanced Organic Chemistry, 5th Ed. Smith and march, Chapter 16, 2001.

* cited by examiner

*Primary Examiner* — Golam M Shameem
(74) *Attorney, Agent, or Firm* — Gerard Devlin; H Eric Fischer

(57) ABSTRACT

Disclosed are novel amino acid derivatives of formula (I) and (II)

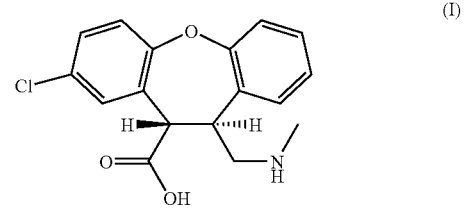

(I)

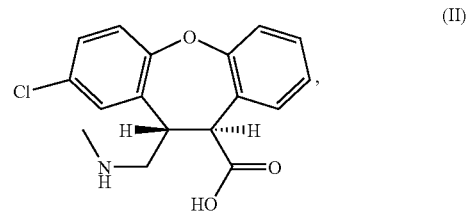

(II)

processes for the preparation thereof, and their use in the preparation of trans-5-chloro-2-methyl-2,3,3a,12b-tetrahydro-1H-dibenz[2,3:6,7]oxepino-[4,5-c]pyrrole.

6 Claims, No Drawings

INTERMEDIATE COMPOUNDS FOR THE PREPARATION OF TRANS-5-CHLORO-2-METHYL-2,3,3A,12B-TETRAHYDRO-1H-DIBENZ[2,3:6,7]-OXEPINO[4,5-C]PYRROLE

This application is a divisional application based on and claiming priority of U.S. patent application Ser. No. 11/399,142 filed Apr. 6, 2006 now U.S. Pat. No. 7,872,147, which application claims priority of U.S. Provisional Patent Application No. 60/669,422, filed Apr. 7, 2005 each of which application is incorporated by reference in its entirety as if fully set forth herein.

This invention relates to novel amino acid derivatives, to processes for the preparation thereof, and to the use of the amino acid derivatives in the preparation of trans-5-chloro-2-methyl-2,3,3a,12b-tetrahydro-1H-dibenz-[2,3:6,7]oxepino[4,5-c]pyrrole.

Trans-5-chloro-2-methyl-2,3,3a,12b-tetrahydro-1H-dibenz[2,3:6,7]oxepino[4,5-c]pyrrole, which is commonly known as asenapine, is a compound having CNS-depressant activity and having antihistamine and antiserotonin activities (See U.S. Pat. No. 4,145,434 to van den Burg). The pharmacological profile of asenapine, its kinetics and metabolism, and the first safety and efficacy studies in human volunteers and in schizophrenic patients have been reviewed (See De Boer et al., *Drugs of the Future*, 18(12), 1117-1123, 1993). It has been established that the maleate salt of asenapine, known as Org 5222, is a broad-spectrum, high potency serotonin, noradrenaline and dopamine antagonist. Asenapine exhibits potential antipsychotic activity and may be useful in the treatment of depression (see international patent application WO 99/32108). A pharmaceutical preparation suitable for sublingual or buccal administration of asenapine maleate has been described (see international patent application WO 95/23600). Asenapine maleate is now the subject of clinical studies, making large scale syntheses of the drug substance necessary.

A general methodology for the preparation of asenapine is described in U.S. Pat. No. 4,145,434. Physical-chemical properties of the drug substance, Org 5222, have been reported (Funke et al., *Arzneim.-Forsch/Drug. Res.*, 40, 536-539, 1990). Additional synthetic methods for the preparation of Org 5222 and radiolabelled derivatives thereof have also been described (Vader et al., *J. Labelled Comp. Radiopharm.*, 34, 845-869, 1994).

The last steps in a known process for the preparation of asenapine (A) are depicted in Scheme I. In this process, the double bond in the enamide, 11-chloro-2,3-dihydro-2-methyl-1H-dibenz[2,3:6,7]oxepino[4,5-c]pyrrol-1-one (III), is reduced by treatment with magnesium in methanol/toluene to produce a mixture of a desired trans-isomer, trans-11-chloro-2,3,3a,12b-tetrahydro-2-methyl-1H-dibenz[2,3:6,7]oxepino[4,5-c]pyrrol-1-one (IV), and an unwanted cis-isomer, cis-11-chloro-2,3,3a,12b-tetrahydro-2-methyl-1H-dibenz[2,3:6,7]-oxepino[4,5-c]pyrrol-1-one (V), in a 1:4 ratio.

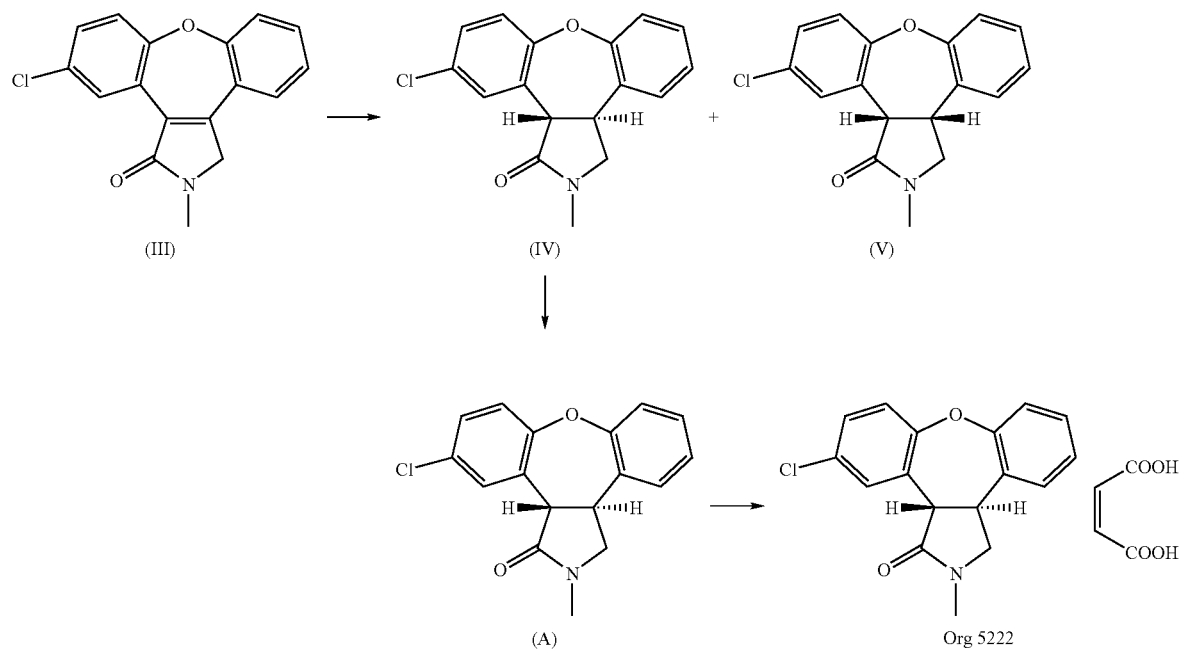

Scheme I

As shown in Scheme II, the unfavorable product ratio can be improved by subsequent partial isomerization of the unwanted cis-isomer (V) into the trans-isomer (IV) using 1,5-diazabicyclo[4.3.0]non-5-ene (DBN), leading to a thermodynamic equilibrium ratio of trans-isomer (IV) to cis-isomer (V) of 1:2. Separation of the trans-isomer (IV) and the cis-isomer (V) is done by chromatography over silica gel. The cis-isomer (V) can be isomerized again using DBN resulting in a 1:2 mixture of compound (IV) and compound (V), from which the trans-isomer (IV) is again separated by chromatography. After further repetition of this cycle at kg scale, recrystallization of the three combined fractions of the trans-isomer (IV) produces trans-11-chloro-2,3,3a,12b-tetrahydro-2-methyl-1H-dibenz[2,3:6,7]oxepino[4,5-c]pyrrol-1-one (IV) in an overall yield of approximately 38% starting from the enamide (III).

Scheme II

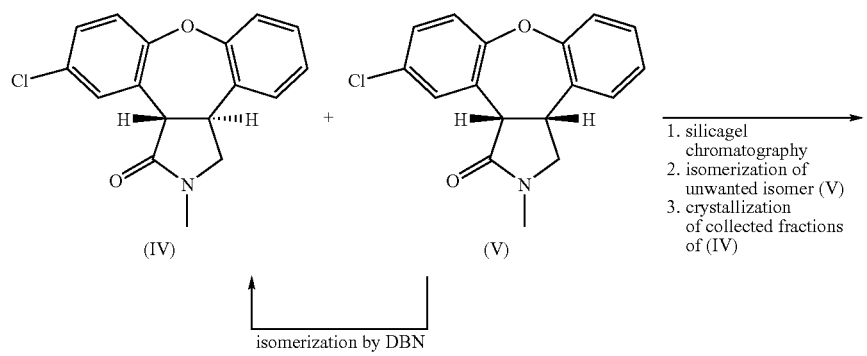

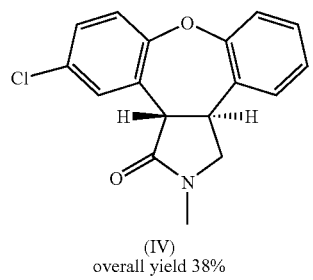

The drawback of the process described above is that it is extremely elaborate and time-consuming, while the final yield of the trans-compound (IV) is only moderate. Therefore there is a need for an improved process for the preparation of the trans-isomer (IV).

Throughout this disclosure, compounds represented by structural formulae having a pair of bold and hashed wedged bonds, as shown, e.g., in compound (IV) of Scheme I, or a pair of bold wedged bonds, as shown, e.g., in compound (V) of Scheme I, refer to "trans" or "cis" diastereoisomers, respectively. Each of the compounds may exist as a single enantiomer having the absolute stereochemical configuration indicated by the wedged bonds, or having the opposite absolute configuration, or as a mixture of enantiomers (e.g., racemate) having the relative stereochemical configuration indicated by the wedged bonds.

The present invention provides a process (Scheme III) in which the mixture of lactams, trans-11-chloro-2,3,3a,12b-tetrahydro-2-methyl-1H-dibenz[2,3:6,7]-oxepino[4,5-c]pyrrol-1-one (IV) and cis-11-chloro-2,3,3a,12b-tetrahydro-2-methyl-1H-dibenz[2,3:6,7]oxepino[4,5-c]pyrrol-1-one (V), is treated in an alcoholic solution comprising an excess of strong alkaline base thereby producing a mixture of trans-8-chloro-10,11-dihydro-11-[(methylamino)methyl]-dibenz[b,f]oxepin-10-carboxylic acid (I) and cis-8-chloro-10,11-dihydro-11-[(methylamino)methyl]-dibenz[b,f]oxepin-10-carboxylic acid (Ia). The ring-opening reaction is stereoselective, resulting in a 10:1 ratio of the trans-isomer (I) to the cis-isomer (Ia). The trans-amino acid derivative (I) is subsequently isolated and cyclized to give trans-11-chloro-2,3,3a,12b-tetrahydro-2-methyl-1H-dibenz[2,3:6,7]oxepino[4,5-c]pyrrol-1-one (IV) with preservation of the trans-stereochemistry. Starting from the enamide derivative (III), the yield of the trans-isomer (IV) is approximately 62%.

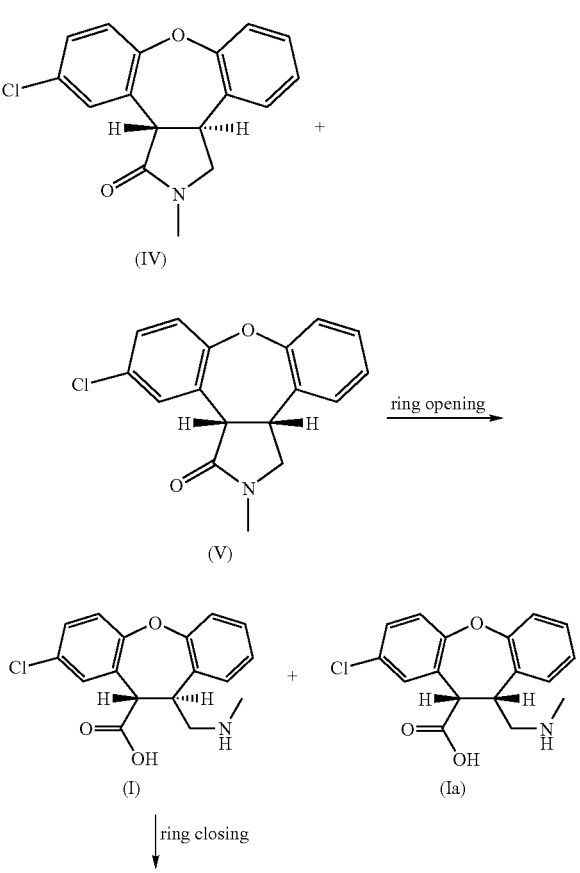

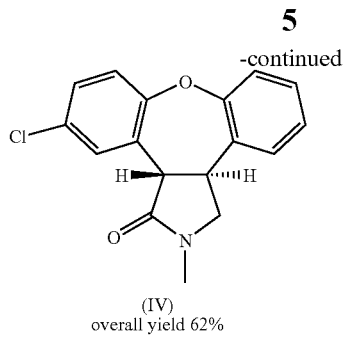

(IV)
overall yield 62%

The starting material for the ring-opening reaction may be a mixture of the trans-isomer (IV) and the cis-isomer (V). Alternatively, the starting material may be the pure cis-isomer (V). The mixture of isomers (IV), (V) may be obtained from compound (III) in accordance with Scheme I, above, or may be obtained in a number of synthesis steps such as described in Example 8.

The hydrolysis of the lactams (IV), (V) can be carried out in an alcoholic solution at reflux temperature in the presence of a stoichiometric excess of a strong alkaline base. Preferred bases include alkali metal hydroxides, such as potassium hydroxide or sodium hydroxide, which are used in 2- to 20-fold or in 10- to 20-fold molar excess based on the amount of the isomers (IV), (V). Useful alcohols include C1 to C6 alkanols, including methanol, ethanol, n-propanol, 2-propanol, n-butanol, and mixtures thereof. The use of higher boiling alcohols, such as n-propanol and n-butanol, appears to provide shorter reaction times for the ring-opening reaction.

After completion of the ring opening reaction, water and ethanol are added and an extractive work up may follow to remove side products. The amino acid derivatives (I), (Ia) are extracted into the water/alcohol phase and acidified to a pH of 1 using hydrochloric acid. Subsequent evaporation of the alcoholic solvents selectively crystallizes the amino acid derivative, trans-8-chloro-10,11-dihydro-11-[(methylamino)methyl]-dibenz[b,f]oxepin-10-carboxylic acid (I), as the hydrochloride salt.

Trans-8-chloro-10,11-dihydro-11-[(methylamino)methyl]-dibenz[b,f]oxepin-10-carboxylic acid (I) may be obtained as the crystalline zwitterion, i.e. free base, when the pH is lowered to 6 instead of 1. Additionally, the zwitterion of trans-8-chloro-10,11-dihydro-11-[(methylamino)methyl]-dibenz[b,f]oxepin-10-carboxylic acid (I) may be prepared from the hydrochloride salt by dissolution in a mixture of methanol and water, neutralization to pH 6 with ammonia or sodium hydroxide solution, and evaporation of the methanol to give the free base (I) as a solid.

The ring-closure reaction (cyclization) of the amino acid derivative (I) to produce the trans lactam derivative (IV) (see Scheme III) may be carried out using the hydrochloride salt or the zwitterionic form by heating a suspension of the amino acid (I) in a solvent, including an aromatic solvent such as toluene or xylene, either with or without an additive to increase the rate of this reaction. Suitable additives are silica gel, aluminum oxide, sodium hydroxide, and sodium acetate. A preferred solvent to carry out the ring closure is toluene; preferred additives are sodium hydroxide and sodium acetate. Sodium acetate is most preferred as it typically results in the shortest reaction time.

In an alternative method for the ring closure, the amino acid derivative (I) is converted into an activated acid form, such as an acid chloride, which upon neutralization with a base, spontaneously cyclizes to the desired lactam (IV).

A further aspect of the invention relates to a process (Scheme IV) for the preparation of trans-2-chloro-10,11-dihydro-11-[(methylamino)methyl]-dibenz-[b,f]oxepine-10-carboxylic acid (II), which is a regioisomer of the amino acid derivative (I) depicted in Scheme III. The process comprises the steps of: (a) reduction of an enamide, 5-chloro-2,3-dihydro-2-methyl-1H-dibenz[2,3:6,7]-oxepino[4,5-c]pyrrol-1-one (VI), to provide a mixture of lactams, trans-5-chloro-2,3,3a,12b-tetrahydro-2-methyl-1H-dibenz[2,3:6,7]oxepino[4,5-c]pyrrol-1-one (VII), and cis-5-chloro-2,3,3a,12b-tetrahydro-2-methyl-1H-dibenz-[2,3:6,7]oxepino[4,5-c]pyrrol-1-one (VIII); (b) hydrolysis of the lactams (VII), (VIII) by treatment in an alcoholic solution with an excess of a strong (alkali) base thereby producing a mixture of the amino acid derivative (II) and its corresponding isomer, cis-2-chloro-10,11-dihydro-11-[(methylamino)methyl]-dibenz[b,f]oxepine-10-carboxylic acid (IIa); and (c) purification of the amino acid derivative (II) from the mixture. Cyclization of the amino acid derivative (II) to the desired lactam (VII), which is a regioisomer of the lactam (IV) depicted in Scheme I, above, and subsequent reduction of the lactam amide group yields asenapine (A).

Scheme IV

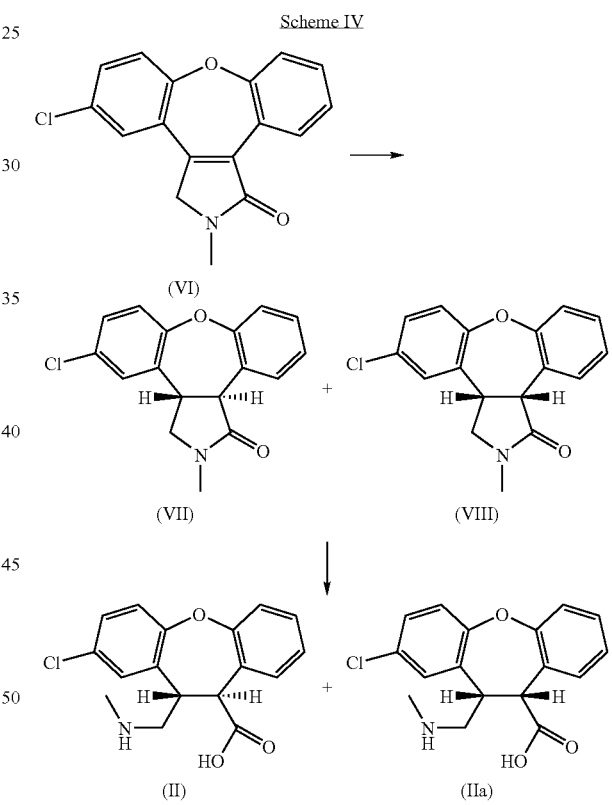

The enamide, 5-chloro-2,3-dihydro-2-methyl-1H-dibenz[2,3:6,7]oxepino[4,5-c]pyrrol-1-one (VI), can for instance be prepared in a number of synthesis steps starting from 4-chlorophenol and methyl 2-bromophenylacetate as described in Example 9.

Another aspect of the invention provides an alternative process for preparing asenapine (A) as shown in Scheme V. The process provides for treatment of an amino acid derivative (I) or (II) with a reducing agent such as borane or lithium aluminum hydride, optionally in combination with a Lewis acid, such as aluminum chloride. This one-pot reaction provides asenapine (A) in a typical yield of 70%.

Scheme V

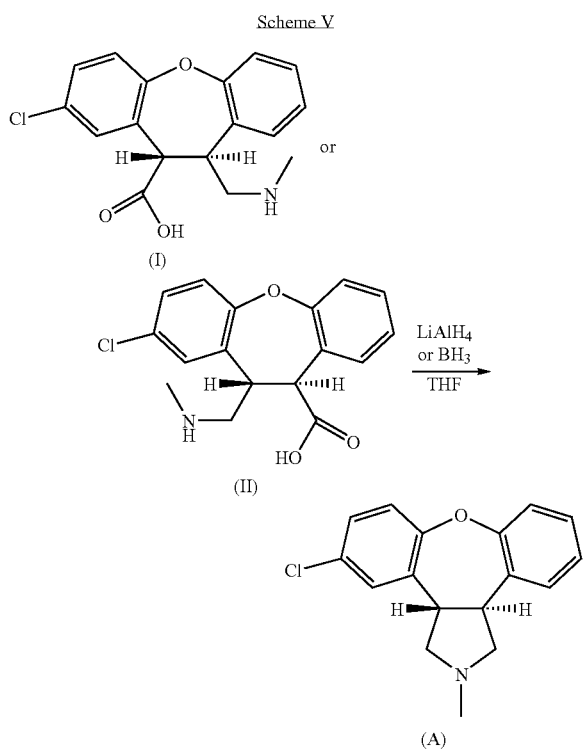

A further aspect of the invention provides the trans-amino acid derivatives of formula (I) or (II), as depicted in Schemes III-V, or the enantiomer of each trans-amino acid derivative having the opposite absolute configuration, or a racemic mixture of each trans-amino acid derivative, or a salt thereof. Suitable salts include alkali metal salts, such as sodium, potassium or lithium salts, or salts obtained from the combination with an organic base, such as trimethylamine, triethylamine and the like. Other suitable salts include acid addition salts, which may be obtained by treating the free compounds (I) or (II) with a mineral acid such as hydrochloric acid or hydrobromic acid, or with an organic acid such as maleic acid, acetic acid, methane sulfonic acid, and the like.

Suitable acid addition salts of asenapine (A) can be obtained from the treatment with a mineral acid such as hydrochloric acid, hydrobromic acid, phosphoric acid and sulfuric acid, or with an organic acid such as for example ascorbic acid, citric acid, tartaric acid, lactic acid, maleic acid, malonic acid, fumaric acid, glycolic acid, succinic acid, propionic acid, acetic acid and methane sulfonic acid. The preferred acid addition salt of asenapine is the maleate salt, i.e. Org 5222.

EXAMPLES

The following examples are illustrative and non-limiting and represent specific embodiments of the present invention. In each of the examples below, the compounds Org 5222, asenapine (A), and all cis- and trans-precursors—e.g., compounds (I), (II), (IV), (V), (VII) and (VIII)—are racemates, and the pairs of bold wedged bonds or bold and hashed wedged bonds used in their structural formulae indicate relative stereochemical configuration.

General Methods

For most of the examples, NMR spectra were recorded on a Bruker DPX 400. $^1$H-NMR chemical shifts (δ) are reported in parts per million (ppm) and are referenced to TMS as an internal standard using the following abbreviations: s (singlet), d (doublet), dd (double doublet) and m (multiplet). Mass spectra were recorded on a PE SCIEX API 165. GC chromatograms were recorded on a HP6890N with a Restek RTX-column.

Example 1

Preparation of trans-11-chloro-2,3,3a,12b-tetrahydro-2-methyl-1H-dibenz[2,3:6,7]oxepino[4,5-c]pyrrol-1-one (IV) following Scheme II A. Mixture of trans-(IV) and cis-11-chloro-2,3,3a,12b-tetrahydro-2-methyl-1H-dibenz[2,3:6,7]oxepino[4,5-c]pyrrol-1-one (V)

Under $N_2$ atmosphere, iodine (4.95 g, 18 mmol) was added to a stirred suspension of magnesium (1.75 gram, 71.87 mmol) in toluene (175 mL). Over a period of 20 minutes, a solution of 11-chloro-2,3-dihydro-2-methyl-1H-dibenz[2,3;6,7]oxepino[4,5-c]pyrrol-1-one (III) (25 gram, 84 mmol; see Vader et al., above) in methanol (175 mL) was added. The reaction mixture was stirred for 35 minutes. Then, over a period of 2 hours, 3 portions of magnesium (1 g, 41.06 mmol) followed by one larger portion of magnesium (2 g, 82.12 mmol) were added. Water (600 mL) and 36% hydrochloric acid (65 mL) were added keeping the temperature below 40° C. Toluene (50 mL) was added, the layers were separated, and the water layer was extracted with toluene (2×100 mL). The combined toluene layers were washed with water (200 mL), dried over magnesium sulfate, filtered and evaporated. This gave a mixture of trans-11-chloro-2,3,3a,12b-tetrahydro-2-methyl-1H-dibenz[2,3:6,7]oxepino[4,5-c]-pyrrol-1-one (IV) and cis-11-chloro-2,3,3a,12b-tetrahydro-2-methyl-1H-dibenz[2,3:6,7]oxepino[4,5-c]pyrrol-1-one (V) (25.5 g, ~100%) in the ratio (IV):(V)=1:4 as determined by $^1$H-NMR and GC.

B. Chromatographic (Silica) Purification of (IV)

5-Diazabicyclo[4,3,0]non-5-ene (DBN, 1.6 L) is added to toluene (400 L) containing a mixture of cis-isomer (V) and trans-isomer (IV) (10 kg in total) and the reaction mixture is stirred for 1 hour at 20° C. Water (200 L) is added and the pH of the aqueous layer is adjusted to pH 4 with acetic acid (approximately 1.0 L). Stirring is continued for 15 minutes and, if necessary, acetic acid is added to adjust the pH to 4.0 (~0.2). The layers are separated. The toluene layer is washed with water (200 L), concentrated to a volume of 25 L and purified by chromatography on silica (100 kg) with toluene (115 L) and toluene:ethyl acetate 95:5 v/v (900 L). The fractions are pooled and fractions containing exclusively compound trans-11-chloro-2,3,3a,12b-tetrahydro-2-methyl-1H-dibenz[2,3:6,7]oxepino[4,5-c]pyrrol-1-one (IV) are combined and concentrated to a volume of 50 L. Fractions containing cis-11-chloro-2,3,3a,12b-tetrahydro-2-methyl-1H-dibenz[2,3:6,7]oxepino[4,5-c]pyrrol-1-one (V) or mixtures of trans-11-chloro-2,3,3a,12b-tetrahydro-2-methyl-1H-dibenz[2,3:6,7]oxepino[4,5-c]pyrrol-1-one (IV) and cis-11-chloro-2,3,3a,12b-tetrahydro-2-methyl-1H-dibenz[2,3:6,7]oxepino[4,5-c]pyrrol-1-one (V) are combined.

C. Repeated Isomerization with DBN

The combined fractions containing cis-isomer (V) are isomerized again using DBN in toluene and subsequent purification by chromatography as described above is repeated twice. Fractions containing exclusively trans-11-chloro-2,3,3a,12b-tetrahydro-2-methyl-1H-dibenz[2,3:6,7]oxepino[4,5-c]pyrrol-1-one (IV) are combined and evaporated in vacuum to give 4.9 kg (49% m/m) of crude trans-11-chloro-2,3,3a,12b-tetrahydro-2-methyl-1H-dibenz[2,3:6,7]-oxepino[4,5-c]pyrrol-1-one (IV). Recrystallization from methanol provides trans-11-chloro-2,3,3a,12b-tetrahydro-2-methyl-1H-dibenz[2,3:6,7]-oxepino[4,5-c]pyrrol-1-one (IV) (3.8 kg, 38%); mp 150.6° C.; $^1$H-NMR (400.13 MHz, CDCl$_3$ relative to TMS) δ 3.03 (d, 3H), 4.03 (m, 1H), 3.53-3.65 (m, 2H), 3.82 (m, 1H), 7.01-7.28 (m, 6H), 7.87 (dd, 1H).

Example 2

Preparation of trans-8-chloro-10,11-dihydro-11-[(methylamino)methyl]-dibenz[b,f]oxepin-10-carboxylic acid (I)

To a solution of cis-11-chloro-2,3,3a,12b-tetrahydro-2-methyl-1H-dibenz[2,3:6,7]oxepino[4,5-c]pyrrol-1-one (V) (2 gram, 6.7 mmol) in ethanol (20 mL), was added potassium hydroxide (3.8 g, 67 mmol). The reaction mixture was heated to reflux for 5 hours. The reaction mixture was evaporated and water was added (50 mL). The water phase was washed with diethyl ether (2×25 mL). The aqueous phase was acidified with concentrated hydrochloric acid to a pH between 5 and 6, resulting in a gum precipitate. Ethyl acetate was added (25 mL), which slowly dissolved the gum and resulted in the formation of fine crystals of the product. The crystals were filtered and dried to give trans-8-chloro-10,11-dihydro-11-[(methylamino)methyl]-dibenz[b,f]oxepin-10-carboxylic acid (I) (1.1 g, 52%); mp 154.4° C.; $^1$H-NMR (399.87 MHz in MeOD relative to TMS) δ 2.09 (s, 3H), 2.45 and 2.66 (2×m, 2H), 3.23 (s, 1H), 3.50 (m, 1H), 3.92 (d, 1H), 6.96-7.20 (m, 6H).

Example 3

Preparation of trans-8-chloro-10,11-dihydro-11-[methylamino)methyl]-dibenz[b,f]oxepin-10-carboxylic acid hydrochloride (I).HCl Potassium hydroxide (333.8 g, 6.30 mole) was added to a mixture of cis-11-chloro-2,3,3a,12b-tetrahydro-2-methyl-1H-dibenz[2,3:6,7]oxepino[4,5-c]pyrrol-1-one (V) and trans-11-chloro-2,3,3a,12b-tetrahydro-2-methyl-1H-dibenz[2,3:6,7]oxepino[4,5-c]pyrrol-1-one (IV) (105 g, 351 mmol, trans/cis ratio 1:3) dissolved in ethanol (1050 mL). The mixture was heated to reflux for 18 hours. Part of the ethanol (500 mL) was evaporated and water was added (1.5 L). The aqueous phase was extracted with toluene (2×750 mL). To the water phase was subsequently added toluene (500 mL) and concentrated hydrochloric acid to adjust the pH to 1. During the addition of hydrochloric acid the temperature rises to 75° C. The water layer was separated and upon cooling crystals of trans-8-chloro-10,11-dihydro-11-[(methylamino)methyl]-dibenz[b,f]oxepin-10-carboxylic acid hydrochloride were formed. The crystals were collected by filtration and dried, giving (I).HCl (84 g, 68%); mp 215° C. (dec.); $^1$H-NMR (399.87 MHz in MeOD relative to TMS) δ 2.65 (s, 3H), 3.30 (s, 2H), 3.95 (m, 1H), 4.32 (d, 1H), 7.11-7.38 (m, 6H).

Example 4

Preparation of trans-11-chloro-2,3,3a,12b-tetrahydro-2-methyl-1H-dibenz[2,3:6,7]oxepino[4,5-c]pyrrol-1-one (IV)

Method A

Trans-8-chloro-10,11-dihydro-11-[(methylamino)methyl]-dibenz[b,f]-oxepin-10-carboxylic acid hydrochloride (I).HCl (55.5 g) and silica gel (55 g) were suspended in xylene (550 mL). The suspension was heated to reflux for 1 night. The reaction mixture was cooled to 65° C. and ethyl acetate (550 mL) was added. The silica gel was filtered off and washed with ethyl acetate (550 mL). The organic phase was evaporated. The crude product was dissolved in methanol (750 mL). The methanol was partly evaporated upon which crystallization of the product takes place. After cooling to 5° C. for 3 hours, the product was obtained by filtration. This yielded trans-11-chloro-2,3,3a,12b-tetrahydro-2-methyl-1H-dibenz[2,3:6,7]oxepino[4,5-c]pyrrol-1-one (IV) (47.8 g, 86%); mp 150.6° C.; $^1$H-NMR (400.13 MHz in CDCl$_3$ relative to TMS) δ 3.03 (d, 3H), 4.03 (m, 1H), 3.53-3.65 (m, 2H), 3.82 (m, 1H), 7.01-7.28 (m, 6H), 7.87 (dd, 1H).

Method B

Trans-8-chloro-10,11-dihydro-11-[(methylamino)methyl]-dibenz[b,f]-oxepin-10-carboxylic acid hydrochloride (I).HCl (50 g, 142 mmol) was suspended in dichloromethane (1 L) and N,N-dimethylformamide (50 mL). To this suspension was added thionyl chloride (50 mL, 84 mmol). After 30 minutes a clear solution was formed. This solution was added dropwise to a cold mixture of methanol (1 L) and triethylamine (158, 1150 mmol). Additional triethylamine (35 mL) was added to adjust the pH to 8. The organic phase was washed with 1N hydrochloric acid (1 L) and with brine (2×1 L). The organic phase was subsequently washed with saturated sodium bicarbonate solution (1 L). The organic phase was dried with magnesium sulfate and evaporated. The crude product (40.7 g) was crystallized from methanol (100 mL). This furnished trans-11-chloro-2,3,3a,12 b-tetrahydro-2-methyl-1H-dibenz[2,3:6,7]oxepino-[4,5-c]pyrrol-1-one (IV) (32 g, 75%); $^1$H-NMR (399.87 MHz in CDCl$_3$ relative to TMS) δ 3.03 (d, 3H), 4.03 (m, 1H), 3.53-3.65 (m, 2H), 3.82 (m, 1H), 7.01-7.28 (m, 6H), 7.87 (dd, 1H).

Example 5

Preparation of asenapine, trans-5-chloro-2,3,3a,12b-tetrahydro-2-methyl-1H-dibenz[2,3:6,7]oxepino[4,5-c]pyrrole (A)

To a first reaction vessel containing tetrahydrofuran (2.4 mL) at 0° C. was added aluminum chloride (167 mg, 1.26 mmol). To the resulting suspension was slowly added lithium aluminum hydride (3.77 mmol). To a second reaction vessel containing THF (4 mL) was added trans-8-chloro-10,11-dihydro-11-[(methylamino)methyl]-dibenz[b,f]oxepin-10-carboxylic acid hydrochloride (I).HCl (0.4 g, 1.26 mmol). At −10° C., the contents of the first reaction vessel were added to the second reaction vessel. After 30 minutes the reaction mixture was quenched with water and extracted with toluene. The toluene was dried with magnesium sulfate and evaporated. This provided crude trans-5-chloro-2,3,3a,12b-tetrahydro-2-methyl-1H-dibenz[2,3:6,7]-oxepino[4,5-c]pyrrole (A) in nearly quantitative yield with a purity of 63%; $^1$H-NMR (400.13 MHz in CDCl$_3$ relative to TMS) δ 2.54 (s, 3H), 3.15 (m, 2H), 3.25 and 3.61 (2×m, 4H), 7.01-7.36 (m, 7H).

Example 6

Preparation of asenapine, trans-5-chloro-2,3,3a,12b-tetrahydro-2-methyl-1H-dibenz[2,3:6,7]oxepino[4,5-c]pyrrole (A)

Aluminum chloride (6.9 kg) is added in portions to tetrahydrofuran (100 L) at 0° C. Stirring is continued and a 10% solution of lithium aluminum hydride in tetrahydrofuran (35.0 L) is added keeping the temperature below 10° C. The mixture is cooled to 0° C. and stirred for 15 minutes. A solution of trans-11-chloro-2,3,3a,12b-tetrahydro-2-methyl-1H-dibenz[2,3:6,7]oxepino[4,5-c]pyrrol-1-one (IV) (10.0 kg) in tetrahydrofuran (100 L) is added to the mixture while keeping the temperature below 15° C. Tetrahydrofuran (5 L) is added, stirring is continued for 1 hour at 10° C., and 0.6 N sodium hydroxide solution (100 L) is added keeping the temperature below 10° C. Stirring is continued for 15 minutes at 20° C. and toluene (150 L) and of water (100 L) are added. Stirring is continued for 15 minutes at 20° C. and the salt layer is separated. The salt layer is extracted with toluene (2×50 L). The combined filtrates are separated and the aqueous layer is extracted with of toluene (50 L). The combined organic layers are evaporated in vacuum at 70° C. to give trans-5-chloro-2,3,3a,12b-tetrahydro-2-methyl-1H-dibenz[2,3:6,7]oxepino [4,5-c]pyrrole (A) (9.4 kg, 99%); $^1$H-NMR (400.13 MHz in CDCl$_3$ relative to TMS) δ 2.54 (s, 3H), 3.15 (m, 2H), 3.25 and 3.61 (2×M, 4H), 7.01-7.36 (m, 7H).

Example 7

Preparation of Asenapine Maleate (Org 5222)

Free base trans-5-chloro-2,3,3a,12b-tetrahydro-2-methyl-1H-dibenz[2,3:6,7]oxepino[4,5-c]pyrrole (A) (1.23 kg) was dissolved in ethanol (2 L) at 60° C. Charcoal (74 g) was added; after stirring for 30 minutes at 60° C., the charcoal was filtered and washed with ethanol (1.2 L). The filtrate was warmed to 65° C. and was maintained at this temperature while a warm (60° C.) solution of maleic acid (554 g) in ethanol (3.5 L) was added over a 15 minute period. The solution was cooled and seeded at 15° C. After 2 hours stirring at 15° C. the suspension was cooled to −10° C. and the crystals were filtered, washed with cold ethanol and dried.

$^1$H-NMR (400.13 MHz in CDCl$_3$ relative to TMS) δ 3.14 (s, 3H), 3.93 (m, 2H), 3.79 and 4.08 (2×m, 4H), 6.24 (s, 2H, vinylic protons of maleic acid), 7.16-7.34 (m, 7H); mass spectrometry m/z 286.1, 229, 220, 201, 194, 166, and 44.

Example 8

Preparation of a mixture of trans-11-chloro-2,3,3a, 12b-tetrahydro-2-methyl-1H-dibenz[2,3:6,7]oxepino [4,5-c]pyrrol-1-one (IV) and corresponding cis-isomer (V)

A. (E and Z)-2-(5-chloro-2-phenoxy-phenyl)-3-hydroxy-acrylic acid methyl ester

A solution of (5-chloro-2-phenoxy-phenyl)-acetic acid methyl ester (167 g, 605 mmol) and methyl formate (173 mL, 2.8 mol) in t-butyl methyl ether (1 L) was cooled to −10° C. To this solution was added potassium t-butoxide (115 g, 1.03 mol) portionwise so that the temperature remained below 0° C. After 30 minutes, the reaction was quenched by addition of 4N aqueous hydrochloric acid (400 mL). The organic layer was separated and washed with water (3×350 mL) and saturated brine (350 mL). The organic fractions were combined and concentrated to dryness and used without purification. The product is 90% E as shown by NMR. $^1$H NMR (400 MHz, CDCl$_3$) 3.6 (s, 3H, E methyl group; Z methyl is at 3.7), 6.8 (d, 1H), 6.9 (m, 2H), 7.0 (t, 1H), 7.2 (m, 3H), 7.3 (m, 2H), 11.8 (d, 1H, E hydroxy proton; Z hydroxy proton is at 4.7).

B. 8-Chloro-dibenz[b,f]oxepin-10-carboxylic acid methyl ester

A slurry of 2-(5-chloro-2-phenoxy-phenyl)-3-hydroxy-acrylic acid methyl ester (210 g, 691 mmol) was heated in pyrophosphoric acid (420 g) to 60° C. After two hours, the reaction was cooled to 20° C. and hexane (250 mL), toluene (500 mL), and water (500 mL) were added to quench the reaction. The organic layer was separated and washed with saturated aqueous sodium bicarbonate (500 mL) and saturated brine (500 mL). The organic fraction was concentrated and the resulting oil was crystallized from n-butanol (500 mL; 20° C. for one hour and −10° C. for two hours), which provided the titled compound as off-white crystals (172 g, 85% yield for steps A and B). $^1$H NMR (400 MHz, CDCl$_3$) 3.9 (s, 3H), 7.1-7.2 (m, 3H), 7.3 (m, 2H), 7.4 (t, 1H), 7.6 (d, 1H), 8.0 (s, 1H).

C. Trans-8-chloro-11-nitromethyl-10,11-dihydro-dibenzo[b,f]oxepine-10-carboxylic acid methyl ester To a 5 L 3-neck round bottom flask was added 8-chloro-dibenz[b,f]-oxepin-10-carboxylic acid methyl ester (305 g, 1.06 mol, 1 eq) followed by THF (1.25 L) and t-butyl-tetramethylguanidine (27 g, 0.15 mol, 0.14 eq). To this solution was added nitromethane (576 g, 9.45 mol, 8.9 eq) in THF (0.5 L) while maintaining a temperature of less than 30° C. The resultant mixture was stirred at room temperature until judged complete by HPLC (overnight, <3% starting material). Once complete, methyl tertiary butyl ether (1.25 L), water (0.6 L) and 1N HCl (0.6 L) were added, the layers were separated, and the aqueous layer was extracted a second time with MTBE (1 L). The combined organic layers were washed with 1N HCl (2×0.6 L) and saturated sodium chloride (0.6 L). After addition of toluene (2 L) the organic fraction was concentrated under vacuum to a volume less than 2 L, toluene (1 L) was added, and the mixture was concentrated to minimum volume. Addition of THF (0.5 L) afforded the titled compound as a light colored solution which was used without further purification (368 g, 1.06 mol, theoretical). HPLC area %: 45% toluene, 48% trans-nitro ester, 6% cis-nitro ester, 1% starting material. HPLC conditions: column—3.5 μm Zorbax SB-Phenyl, 3 mm×150 mm; solvent—gradient from 55% water (0.1% HOCl$_4$)/45% methanol (0.1% HOCl$_4$) to 100% methanol (0.1% HOCl$_4$) in 10 minutes and hold for 2 minutes; flow 0.5 mL/minute; detection at 210 nm.

D. 11-Aminomethyl-8-chloro-10,11-dihydro-dibenzo[b,f]oxepine-10-carboxylic acid methyl ester and 11-chloro-2,3,3a,12b-tetrahydro-1H-dibenz-[2,3:6,7]oxepino[4,5-c]pyrrol-1-one An aqueous slurry of A7000 sponge nickel catalyst (111.74 g/60 mL, containing approximately 60.36 g of catalyst on a dry basis) was washed by adding THF (40 mL), agitating, and decanting the supernatant. The catalyst slurry was then charged to a 1500-mL Hastelloy-C stirred autoclave with the aid of THF (200 mL). The vessel was sealed, purged with hydrogen, and pressurized to about 50 psig with hydrogen. The mixture was stirred at 1100 rpm at room temperature and a solution of trans-8-chloro-11-nitromethyl-10,11-dihydro-dibenzo[b,f]oxepine-10-carboxylic acid methyl ester (ca. 369 g, 1.06 mol in 500 mL THF) diluted to 850 mL with THF was added at a rate of about 3.1 mL/minute over the course of about 4.5 hours. The temperature of the reaction mixture rose from the exotherm but was maintained between 20 to 32° C. by the application of an external water cooling bath. The total pressure in the reactor was maintained at 50 to 60 psig by supplying hydrogen on-demand through a pressure regulator from high-pressure reservoir of known volume. After the addition of the starting material was complete, the addition system was rinsed with THF (2×25 mL) into the reactor. The completed reaction mixture was stirred at room temperature under about 60 psig hydrogen overnight. After venting of the hydrogen, the reaction mixture was cautiously vacuum filtered and the cake washed with THF (Note: care is required to avoid drying of the catalyst cake in air) to afford a mixture of the titled compounds (1.06 mol, theoretical) as a THF solution. This material was used without further purification. HPLC area % assay: the combined filtrate and washings (1266 g) was devoid of starting material, and consisted of a mixture of the expected amino ester and cis- and trans-lactams. HPLC conditions: same as step C, above.

E. Trans-11-chloro-2,3,3a,12b-tetrahydro-2-methyl-1H-dibenz[2,3:6,7]-oxepino[4,5-c]pyrrol-1-one (IV) and corresponding cis-isomer (V)

To a 5 L 3-neck round bottom flask equipped with mechanical stirring was added THF (1.0 L) followed by the hydrogenation product from step D (1.06 moles in about 0.8 L THF). The contents of the vessel were subsequently cooled to 0° C. Solid potassium t-butoxide (178 g, 1.59 mol, 1.5 eq) was then added portion-wise while maintaining a temperature of less than 5° C. The resulting dark suspension was stirred at less than 5° C. until complete consumption of the amino ester, as determined by HPLC. Dimethyl sulfate (170 mL, 1.8 mol, 1.7 eq) was then slowly added while maintaining a temperature of less than 5° C., giving an orange suspension. The contents of the vessel were stirred at less than 5° C. until the reaction was complete by HPLC (<5% des-methyl lactam) at which time ammonium hydroxide (0.5 L) in water (1.0 L) was added to decompose any remaining dimethyl sulfate. The mixture was gradually warmed to room temperature and stirred overnight. Ethyl acetate (0.5 L) was added and the layers were separated. The resultant aqueous layer contained product solids that were extracted into ethyl acetate (2.5 L, 0.5 L) at elevated temperature (55° C.). The combined organic layers were concentrated in vacuo to a volume of less than 1 L; octane (0.25 L) was added, and the resultant suspension was warmed to 50° C. followed by cooling to 0° C. The suspension was filtered, washed with octane and dried under vacuum at 50° C. to afford predominantly the cis-isomer (V) (215.7 g, 68% yield from oxepine ester). HPLC area %: 1.6% unknown, 98.4% cis-isomer (V), and trace trans-isomer (IV). The filtrate from the above isolation was concentrated under vacuum, MTBE was added, and the mixture was heated to reflux. The resultant suspension was cooled to room temperature, filtered, and dried to afford a mixture of cis- and trans-isomers, (V) and (IV), respectively (28.9 g, 9% yield). HPLC area %: 7.9% cis-isomer (V), 92.1% trans-isomer (IV). The filtrate from the second isolation was concentrated under vacuum, MTBE (500 mL) and octane (50 mL) were added, and the mixture heated to reflux. The resultant suspension was cooled to 0° C., filtered, and dried to afford a mixture of cis- and trans-isomers, (V) and (IV), respectively (12.2 g, 4% yield). HPLC area %: 4.8% cis-isomer (V), 2.4% unknown, 92.7% trans-isomer (IV). HPLC conditions: same as step C, above. Total yield of the titled compounds was 256.8 g, 81% from trans-8-chloro-11-nitromethyl-10,11-dihydro-dibenzo[b,f]-oxepine-10-carboxylic acid methyl ester (step C).

Example 9

Preparation of asenapine via the lactam trans-5-chloro-2,3,3a,12b-tetrahydro-2-methyl-1H-dibenz[2,3:6,7]oxepino[4,5-c]pyrrol-1-one (VII)

A: [2-(4-Chloro-phenoxy)-phenyl]-acetic acid (IX)

Methyl 2-bromophenylacetate (47.0 grams 216.3 mmol) and 4-chlorophenol (27.8 grams, 215.8 mmol) were dissolved in dioxane (790 ml) while warming to 50° C. To the resulting solution were added, under stirring in an inert nitrogen atmosphere, cesium carbonate (141 grams, 432.2 mmol) and copper(I) chloride (18.56 g, 86.2 mmol). Finally, N,N-dimethylglycine (4.46 grams, 43.2 mmol) was added to the green suspension. The reaction mixture was heated at 110° C. (reflux temperature) for 4 days while stirring. The reaction mixture was filtered over dicalite, which was washed with dioxane (40 ml). The dioxane was removed in vacuo to leave a brownish oil. Ethyl acetate (100 ml) was added to the oil and the pH of the resulting mixture was adjusted to 1 by addition of 1 M HCl (300 ml). The organic phase was washed with saturated brine (300 ml), dried on magnesium sulphate and then concentrated under vacuum to yield 57.2 grams (206 mmol; 95%) of 2-(4-chloro-phenoxy)phenyl]-acetic acid methyl ester as a brown oil. The oil was dissolved in methanol (250 ml), whereupon KOH (16.2 grams; 1.4 eq) was added. The resulting solution was heated for 3 h at 60° C. The reaction mixture was cooled and the methanol (200 ml) was removed under vacuum. To the residue water (100 ml) was added and the pH was adjusted to 1 by addition of 1M HCl (25 ml). The resulting crystals were filtered off and dried in vacuum at 40° C. to yield 47.3 grams (180 mmol; 87%) of [2-(4-chloro-phenoxy)-phenyl]-acetic acid (IX).

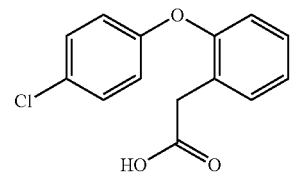

(IX)

B: Methyl-N-[2-(4-chloro-2-phenoxyphenyl)-1-oxethyl]-N-methylglycinate (X)

[2-(4-chloro-phenoxy)-phenyl]-acetic acid (IX) (47.3 grams; 180 mmol) was suspended in toluene (140 ml) at 48° C. To this suspension dimethylformamide (4.0 ml) and SOCl$_2$ (19.8 ml; 271 mmol; 1.5 eq) in toluene (18 ml) were added. After 10 min the reaction mixture was concentrated under vacuo and stripped twice with toluene, to yield a brownish oil of [2-(4-chlorophenoxy)-phenyl]-acetyl chloride. The oil was suspended in toluene (75 ml). To the suspension was added at 5° C. a solution of sarcosine methylester (30.3 grams 217 mmol) and triethylamine (57 ml) in a mixture of dimethylformamide (236 ml) and toluene (47 ml). The brownish suspension was stirred for 2 hours at room temperature. To the reaction mixture water (750 ml) was added and the mixture was extracted twice with ethyl acetate (500 ml). The organic phase was washed with saturated brine (700 ml) and dried on magnesium sulphate. The solvent was removed in vacuum to yield methyl-N-[2-(4-chloro-2-phenoxyphenyl)-1-oxethyl]-N-methylglycinate (X) (61.3 grams, 202 mmol) as a brownish oil.

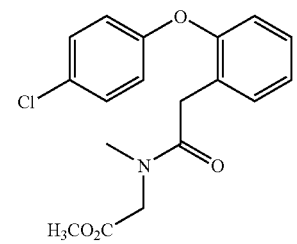

(X)

C: 3-[2-(4-Chloro-phenoxy)-phenyl]-1-methyl-pyrrolidine-2,4-dione (XI)

To a suspension of tert.-BuOK (21.7 grams; 193 mmol) in toluene (240 ml) was added under nitrogen at 20° C. a solution of compound (X) (61.3 grams), as obtained under (B), in toluene (240 ml). The resulting suspension was stirred overnight. To the brownish suspension water (750 ml) was added. The solution was extracted 3 times with ethyl acetate (3×300 ml). The combined organic phases were washed with water (200 ml). The pH of the water-phase was adjusted with HCl to 1. The obtained crystals were stirred for 3 hours before filtering off. The crystals were dried under vacuum at 40° C. to leave 40.2 grams (127 mmol, 72%) of 3-[2-(4-chloro-phenoxy)-phenyl]-1-methyl-pyrrolidine-2,4-dione (XI). GC-purity: 96%.

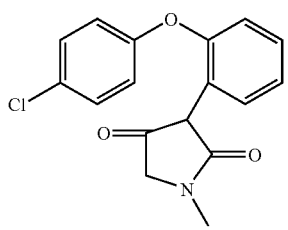

(XI)

D: 5-Chloro-2,3-dihydro-2-methyl-1H-dibenz[2,3;6,7]oxepino[4,5-c]pyrrol-1-one (VI)

$P_2O_5$ (90 grams) was added in portions to $H_3PO_4$ (90 grams) while maintaining the temperature below 140° C. The mixture was heated at 115° C. for 1.5 hour, whereupon 3-[2-(4-chloro-phenoxy)-phenyl]-1-methyl-pyrrolidine-2,4-dione (XI) (30 grams; 95 mmol) was added. The resulting mixture was stirred for 4 days at 115° C. to 130° C. with extra $P_2O_5$ (in total 5 portions of 5 grams each were added). The mixture was poured into water (200 ml) and the resulting precipitate was stirred overnight. The mixture was extracted with dichloromethane (250 ml) and washed with sat. $NaHCO_3$ (pH=7). After drying on magnesium sulphate the solvent was removed under vacuum. The resulting crude product was dissolved in methanol (520 ml) at 70° C. Following removal of part of the methanol by evaporation the product crystallized. The mixture was stirred overnight at −12° C. The crystals were filtered and dried to provide 5-chloro-2,3-dihydro-2-methyl-1H-dibenz[2,3;6,7]oxepino[4,5-c]pyrrol-1-one (VI) (16.4 grams, 55 mmol; 58%), purity according to GC 92%. $^1$H-NMR (400 MHz, CDCl$_3$): 3.2 (s, 3H), 4.3 (s, 1H), 3.8 (m, 1H), 7.2-7.4 (m, 6H), 8.2 (dd, 1H).

E: trans-5-Chloro-2,3,3a,12b-tetrahydro-2-methyl-1H-dibenz[2,3:6,7]oxepino[4,5-c]pyrrol-1-one (VII) and cis-5-chloro-2,3,3a,12b-tetrahydro-2-methyl-1H-dibenz[2,3;6,7]oxepino[4,5-c]pyrrol-1-one (6) (VIII)

Under N$_2$ atmosphere iodine (3.0 grams, 11 mmol) was added to a stirred suspension of magnesium (1.22 grams, 50 mmol) in toluene (82 ml). Over a period of 20 minutes a solution of 5-chloro-2,3-dihydro-2-methyl-1H-dibenz[2,3;6,7]oxepino[4,5-c]pyrrol-1-one (VI) (16.4 gram, 55 mmol) in methanol (57 ml) was added. The reaction mixture was stirred for 35 minutes. Then over a period of 2 hours 3 portions of magnesium (2×500 mg, 41.06 mmol) followed by one larger portion of magnesium (4×500 mg, 82.12 mmol) were added. Water (600 ml) and conc. hydrochloric acid (65 ml) were added while keeping the temperature below 40° C. Toluene (50 ml) was added, the layers were separated and the water layer was extracted twice with toluene (100 ml). The combined toluene layers were washed with water (200 ml), dried on magnesium sulphate, filtered and evaporated. This gave a mixture of trans-5-chloro-2,3,3a,12b-tetrahydro-2-methyl-1H-dibenz[2,3:6,7]oxepino[4,5-c]pyrrol-1-one (VII) and cis-5-chloro-2,3,3a,12b-tetrahydro-2-methyl-1H-dibenz[2,3:6,7]oxepino[4,5-c]pyrrol-1-one (6) (VIII) (13.6 grams, 82%) in the ratio (VII):(VIII)=3:7 as determined by $^1$H-NMR and GC.

$^1$H-NMR (400 MHz, CDCl$_3$): 2.9 (s, 3H, cis), 3.0 (s, sH, trans), 4.0 (m, 1H), 3.53-3.65 (m, 2H), 3.8 (m, 1H), 7.0 (d, 1H, trans), 7.15-7.28 (m, 6H), 7.4 (dd, 1H, cis), 7.9 (dd, 1H, trans).

F: trans-2-Chloro-10,11-dihydro-11-[(methylamino)methyl]-dibenz[b,f]oxepin-10-carboxylic acid hydrochloride (II)

The mixture of lactams (VII) and (VIII) (13.6 grams, 45 mmol, trans/cis ratio 1:2.3), obtained as described under E, was dissolved in ethanol (140 ml). To the solution potassium hydroxide was added (43 grams, 811 mmol), whereupon the mixture was heated to reflux for 18 hours. Part of the ethanol (60 ml) was evaporated and water was added (200 mL). The aqueous phase was extracted twice with toluene (100 ml). Subsequently toluene (100 ml) was added to the water phase, followed by concentrated hydrochloric acid to adjust the pH to 1. During the addition of hydrochloric acid the temperature rises to 75° C. The water layer was separated and upon cooling the product crystallized. The crystals were collected by filtration and dried to provide trans-2-chloro-10,11-dihydro-11[(methylamino)methyl]-dibenz[b,f]oxepin-10-carboxylic acid hydrochloride (II) (3.75 grams, 10.6 mmol, 22%).

M.p: 203.1° C. $^1$H-NMR (400 MHz, MeOD): 2.6 (s, 3H), 3.3 (s, 2H), 3.9 (m, 1H), 4.4 (d, 1H), 7.10-7.36 (m, 6H).

G: trans-5-Chloro-2,3,3a,12b-tetrahydro-2-methyl-1H-dibenz[2,3:6,7]oxepino[4,5-c]pyrrol-1-one (VII)

To a suspension of trans-2-chloro-10,11-dihydro-11-[(methylamino)methyl]-dibenz[b,f]oxepin-11-carboxylic acid hydrochloride (II) (2.00 grams, 5.65 mmol) in toluene (15 ml) was added sodium acetate (0.55 grams, 6.70 mmole). The suspension was heated for 2 hours at reflux. The mixture was filtered and the filtrate was concentrated under vacuum at 50° C. to leave a brownish oil (1.49 grams, 4.97 mmol, 89%), shown to be a mixture of trans (VII) and cis (VIII) in the ratio (VII):(VIII)=8:2 as determined by $^1$H-NMR and GC. Crystallization from methanol (20 ml) gave pure trans-5-chloro-2,3,3a,12b-tetrahydro-2-methyl-1H-dibenz[2,3:6,7]oxepino[4,5-c]pyrrol-1-one (VII) in a yield of 0.80 gr (2.67 mmol, 47%).

M.p: 148.4° C. $^1$H-NMR (400 MHz, CDCl$_3$): 3.1 (s, 3H, trans), 4.2 (m, 1H), 3.53-3.65 (m, 2H), 3.8 (m, 1H), 7.0 (d, 1H0, 7.15-7.28 (m, 5H), 7.8 (dd, 1H).

H: Asenapine: trans-5-chloro-2,3,3a,12b-tetrahydro-2-methyl-1H-dibenz[2,3:6,7]oxepino[4,5-c]pyrrole (A)

Aluminum chloride (65.7 mg) was added in portions to tetrahydrofuran (5 mL) at 0° C. Under stirring a 10% solution of lithium aluminum hydride in tetrahydrofuran (1.35 mL) was slowly added while keeping the temperature below 10°

C. The mixture was cooled to 0° C. and stirred for 15 minutes. A solution of trans-5-chloro-2,3,3a,12b-tetrahydro-2-methyl-1H-dibenz[2,3:6,7]oxepino[4,5-c]pyrrol-1-one (VII) (0.40 grams) in tetrahydrofuran (4 mL) was added to the mixture while keeping the temperature below 15° C. Stirring was continued for 2 hours at 10° C., whereupon 0.5 N sodium tartrate solution (15 mL) was added while keeping the temperature below 10° C. Stirring was continued for 15 minutes at 20° C. The salt layer was extracted twice with a toluene:ethyl acetate (8:2) mixture (25 mL). The combined organic layers were dried on magnesium sulphate, filtered and evaporated in vacuo to yield 0.36 grams (94%) of trans-5-chloro-2,3,3a,12b-tetrahydro-2-methyl-1H-dibenz[2,3:6,7]oxepino[4,5-c]pyrrole (A).

$^1$H-NMR (400 MHz, CDCl$_3$): 2.6 (s, 3H), 3.1 (m, 2H), 3.2 (m, 2H), 3.6 (m, 2H), 7.01-7.36 (m, 7H).

The invention claimed is:

1. A process for preparing a trans-amino acid derivative of formula I,

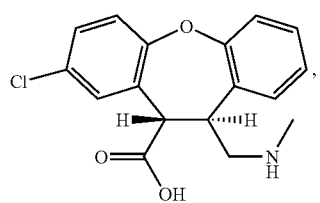
(I)

the process comprising reacting a mixture of lactams of formula IV and Formula V,

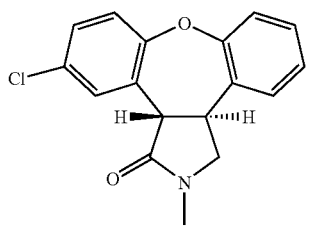
(IV)

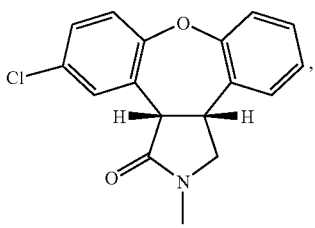
(V)

with a base in the presence of an alcohol.

2. A process for preparing a trans-amino acid derivative of formula II,

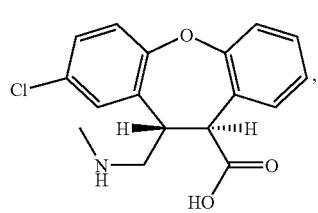
(II)

the process comprising reacting a mixture of lactams of formula VII and formula VIII,

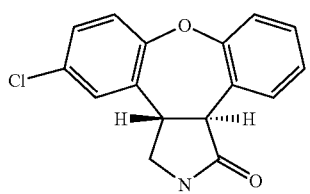
(VII)

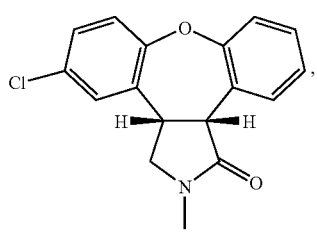
(VIII)

with a base in the presence of an alcohol.

3. The process of claim 1, wherein the base is an alkaline base that is present in stoichiometric excess, and the alcohol is a C1 to C6 alkanol.

4. The process of claim 2, wherein the base is an alkaline base that is present in stoichiometric excess, and the alcohol is a C1 to C6 alkanol.

5. The process of claim 1, wherein the base is potassium hydroxide and the alcohol is ethanol.

6. The process of claim 2, wherein the base is potassium hydroxide and the alcohol is ethanol.

* * * * *